United States Patent [19]

Briggs

[11] Patent Number: 5,749,169
[45] Date of Patent: May 12, 1998

[54] USE OF THE INDETERMINATE GAMETOPHYTE GENE FOR MAIZE IMPROVEMENT

[75] Inventor: Steven P. Briggs, Des Moines, Iowa

[73] Assignee: Pioneer Hi-Bred International, Inc., Johnston, Iowa

[21] Appl. No.: 488,277

[22] Filed: Jun. 7, 1995

[51] Int. Cl.$^6$ .................... C12N 15/29; C12N 15/82; A01H 1/00; A01H 5/00
[52] U.S. Cl. .................... 47/58; 800/200; 800/205; 800/230; 800/235; 800/250; 800/DIG. 56; 435/6; 435/172.1; 435/172.3
[58] Field of Search .................... 47/58; 800/230, 800/200, 205, 235, 250, DIG. 56; 435/6, 172.1, 172.3

[56] References Cited

FOREIGN PATENT DOCUMENTS

| | | |
|---|---|---|
| 0 405 511A3 | 6/1990 | European Pat. Off. |
| 0 636 310 | 2/1995 | European Pat. Off. ......... A01H 1/04 |
| WO 90/09450 | 8/1990 | WIPO |

OTHER PUBLICATIONS

Kindiger et al. Generation of Haploids in Maize: A Modification of the Indeterminate Gametophyte (ig) System. Crop Science, vol. 33, pp. 342–344, Mar.–Apr. 1993.

McLaughlin et al. Cloning of a Mutable bz2 Allele of Maize by Transposon Tagging and Differential Hybridization. Genetics 117: 771–776, Dec. 1987.

Kasha et al. Haploidy in Crop Improvement, *Cytogenetics of Crop Improvement*/Macmillan, pp. 19–68, 1983.

W. Nitzsche et al., "Haploids in Plant Breeding", *Advances in Plant Breeding: Supplements to Journal of Plant Breeding*, Verlag Paul Parey pp. 1–101 (1977).

E.H. Coe, Jr., "A Line of Maize with High Haploid Frequency", *The American Naturalist* 93(873): 381–382 (1959).

S.T. Chalyk et al., "Comparison of Haploid and Diploid Maize (*Zea mays* L.) Plants with Identical Genotypes", *J. Genet. & Breed.* 47: 77–80 (1993).

J.L. Kermicle, "Androgenesis Conditioned by a Mutation in Maize", *Science* 166: 1422–1424 (1969).

B. Lin, "Megagametogenetic Alterations Associated with the Indeterminate Gametophyte (ig) Mutation in Maize", *Rev. Brasil. Biol.* 41(3): 557–563 (1981).

J. Kermicle et al., "Location of Indeterminate Gametophyte (ig) on Chromosome 3", *Maize Genet. Coop. Newsl.* 54: 84–85 (1980).

T.M. Choo, "Doubled Haploids for Studying the Inheritance of Quantitative Characters", *Genetics* 99: 525–540 (1981).

Jerry L. Kermicle, "Indeterminate Gametophyte (ig): Biology and Use", *The Maize Handbook*, Freeling et al. Eds., 388–393 (1994).

James A. Birchler, "Practical Aspects of Haploid Production", *The Maize Handbook*, Freeling et al. Eds., 387–388 (1994).

A. R. Henson et al., "R–Navajo Kernel Color Expression as a Selection Criterion in a Sugary 2, Opaque 2 Maize Synthetic", *Crop Science*, 30:584–587 (1990).

A. Marion–Poll, et al., (Transposition of the Maize Autonomous Element Activator in Transgenic *Nicotiana plumbaginifolia* Plants, *Mol Gen Genet* 238:209–217 (1993).

V. Walbot, "Stratagies For Mutagenesis and Gene Cloning Using Transposon Tagging and T–DNA Insertional Mutagenesis", *Annu. Rev. Plant Phys.* 43:49–82 (1992).

P.S. Chomet, "Transposon Tagging with Mutator", *The Maize Handbook*, Freeling et al. Eds., 243–249 (1994).

Primary Examiner—Douglas W. Robinson
Assistant Examiner—Thomas Haas
Attorney, Agent, or Firm—Foley & Lardner

[57] ABSTRACT

A methodology for ascertaining gene function entails selection of mutations in androgenetic haploids which are produced by fertilizing a maize plant carrying the indeterminate gametophyte gene (ig) with pollen obtained from a mutagenized plant. Genes that control quantitative characters can be identified, for example, by fertilizing a first inbred carrying the ig gene with pollen from a second inbred that has been mutagenized. Changes in the phenotype of the hybrid progeny then are identified and characterized. A method for direct selection of androgenetic haploids is provided.

8 Claims, No Drawings

1

USE OF THE INDETERMINATE GAMETOPHYTE GENE FOR MAIZE IMPROVEMENT

BACKGROUND OF THE INVENTION

1. Field of the Invention

The present invention relates to methods of ascertaining gene function in which mutations are selected in androgenetic haploids that are produced as the result of fertilization of a maize plant carrying the indeterminate gametophyte gene (ig) with pollen obtained from a mutagenized plant. The present invention also relates to identification of genes controlling quantitative characters in which the ig gene and mutation are in different inbred lines and the mutation is identified in the hybrid resulting from the cross of these inbreds. The present invention also relates to maize plants that carry the ig gene that produce androgenetic haploids at high frequency. The present invention also relates to a method of directly selecting androgenetic haploids produced from ig maize plants.

2. Background

Genes that affect a given trait are recognized by their mutant phenotypes and therefore methods that enhance the ability to observe such mutants will accelerate the discovery of the corresponding genes. Conventional diploid genetics requires that recessive mutations, which account for the vast majority of all mutations, be observed in the homozygous condition. Therefore, mutations which are brought into the zygote by one of the gametes cannot be observed in the immediate diploid generation. The heterozygous individual must be selfed or put through a series of sibling crosses to obtain the homozygous mutant.

Typically, the plant breeder screens 20 progeny from each F1 individual to detect mutations that were transmitted to the F1 plant from one of its parents. In order to screen for mutations in 1000 gametes, the plant breeder generally examines 20×1000 or 20,000 $F_2$ progeny. Many experiments are impracticable in view of the 20× multiplier and the large number of plants that must be screened in the $F_2$.

Certain advantages associated with use of haploids in a plant breeding program for crop improvement have been recognized as evidenced by Kasha et al., "Haploidy in Crop Improvement" in CYTOGENETICS OF CROP IMPROVEMENT 19–68 (Macmillan 1983), or Nitzsche et al., "Haploids in Plant Breeding" in ADVANCES IN PLANT BREEDING: SUPPLEMENTS TO JOURNAL OF PLANT BREEDING 1-101 (Verlag Paul Parey 1977). Some of these advantages include rapid production of homozygous inbred lines through haploidization and chromosome doubling, mutation studies for recovery of recessive mutations in homozygous backgrounds, transfer of genes from polyploid to diploid species, or incorporation of nuclei into alien cytoplasm using androgenetic haploids.

Both Kasha et al. and Nitzsche et al. also review known strategies for production of haploids. Coe, *Amer. Natur.* 93: 38 (1959) describe an inbred line Stock 6 that produces up to 3% haploids. Chalyk et al., *J. Genet. & Breed.* 47: 77–80 (1993) describe production of maternal maize haploids using the haploid-inducer line ZMS (Zarodyshevy Marker Saratovsky). ZMS was used as the pollen parent and haploids were produced at a frequency of 0.55 to 3.43% of maize plants observed.

The maize ig gene induces haploids of both male (androgenetic) and female (gynogenetic) origin. The ig gene was first described by Kermicle, *Science* 166: 1422–24 (1969), as arising spontaneously in the highly inbred Wisconsin-23 (W23) strain. The presence of ig increases the occurrence of paternal haploids from the natural spontaneous frequency of about 1 per 80,000 to a frequency of 1 to 3% of maize plants observed. The ig gene is essential for the normal growth and development of the gametophyte and loss of function of the ig gene causes too many or too few nuclei to be produced. In ig lines the developing megagametophyte is released from its normal three mitotic divisions. Lin, *Rev. Brasil. Biol.* 41(3): 557–63 (1981), observed that the presence of ig allows the occurrence of a variable number of mitotic divisions and some of the nuclei degenerate. Following fertilization of the megagametophyte, sperm nuclei occasionally develop androgenetically into paternal haploid embryos. Embryonic development of sperm nuclei in maternal cytoplasm results in the formation of androgenetic haploids. Kermicle et al., *Maize Genet. Coop. Newsl.* 54: 84–85 (1980), determined that the ig allele is positioned in the long arm of chromosome 3 at 90 cM from the most distal locus in the short arm designated $g^2$.

The infrequent occurrence of haploids from ig germplasm remains an obstacle to the reliable identification and propagation of haploids. This obstacle is compounded by the difficulty of maintaining the stock in a homozygous (igig) condition. In an attempt to enhance the frequency of haploids and overall utility of the system, Kindiger et al., *Crop Science* 33: 342–44 (1993), developed a tertiary trisomic stock (A A B-A) by utilizing a simple B-A translocation designated TB-3Ld. The ig allele was placed in a tertiary (B-A) trisomic modified W23 background the frequency of haploidy increased to as high as 8% in some backgrounds. The development of tertiary trisomic ig ig B-3Ld(Ig) stock also allowed for rapid and successful development of cytoplasmic male sterile (CMS) stocks designed to carry ig in a homozygous condition.

The trisomic method of increasing the frequency of ig-induced haploid plants suffers certain distinct disadvantages. Progeny testing must be undertaken to maintain the translocation. In addition to this complexity, haploid progeny must then be selected.

To aid in the identification of maternal or paternal haploids, the ig gene has been combined with $r^g$ (recessive colorless seeds and green plants), and in separate stocks, with the dominant marker $R^{nj}$ (purple pigmented kernel crown, scutellum, plumule and seedlings) for identification of haploids of maternal or paternal origin. For example, from crosses of ig $R^{nj}$ with Ig $r^g$pollen, the haploids of paternal origin will have colorless scutellum and green seedlings. Typically in maize, the Purple Embryo Marker stock (PEM) of the genotype b pl A C $R^{nj:cu\ du}$ pr $p^{wr}$ is used to detect ig-induced haploids. $R^{nj:cu\ du}$ in combination with the dominant pigment-conditioning genes A and C cause red or purple pigmentation of the aleurone, primarily on the crown portion of the kernel, and a deep purple pigmentation in the embryo. For the detection of ig-induced androgenetic haploids, a PEM-ig stock is used as the seed parent in crosses with the donor line or breeders stock. The desired haploids have a white embryo and colored aleurone. A serious disadvantage of the PEM system is that igig females produce a high proportion of defective and small kernels making it difficult to identify ig-induced haploids that have a white embryo and colored aleurone.

A need therefore exists for a strategy that facilitates identification of androgenetic haploids among the progeny produced from crosses with ig plants. In addition, methodology is needed that employs androgenetic haploids to facilitate characterization of gene function, including the

3 identification of transposon-tagged genes, enhancers, suppressors and genes that control quantitative characters.

SUMMARY OF THE INVENTION

Accordingly, it is an object of the present invention to provide a method for direct selection of androgenetic haploids in which the $R^{nj}$ gene is only expressed in androgenetic haploids and therefore the androgenetic haploids are identified and selected as seeds with colored embryos.

Another object of the present invention is to provide a method for ascertaining gene function in which the ig plant is crossed as the female to a plant that carries transposon-induced mutations to facilitate the identification and characterization of the mutated gene in a haploid background.

Yet another object of the present invention is to provide a method of identifying and characterizing enhancers and suppressors in which a mutant plant population is produced that is (i) homozygous for a first mutation that causes a first mutant phenotype induced by chemical mutagenesis or insertion of a first transposable element and (ii) carries a second mutation produced by the insertion into its genome of a second transposable element. Pollen from this mutant plant population is used to pollinate plants capable of producing paternal haploid offspring to produce a plurality of haploid $F_1$ progeny plants which contain genetic material only from mutant plant population and which is screened for a change in the first mutant phenotype.

It is a further object of the present invention to provide a method of ascertaining gene function controlling quantitative characters in which a first inbred is mutagenized and pollen from this mutagenized first inbred is used to fertilize an ig plant to produce androgenetic haploids. The haploids then are fertilized by pollen from a second inbred to produce seed that is isogenic. The seed is screened for mutant hybrids.

An object of the present invention is to provide a method for ascertaining gene function, comprising the steps of selecting two parent plants, wherein the first plant is capable of producing paternal haploid offspring, and wherein the second plant carries at least one mutation produced by the insertion into its genome of a transposable element; crossing the first plant as a female parent with the second plant as the male parent to produce a plurality of haploid $F_1$ progeny plants which contain genetic material only from the second plant; screening the haploid offspring for the simultaneous presence of a transposable element and a mutant phenotype which differs from a parental phenotype; and cloning DNA from the mutant haploid that is associated with insertion of the transposon.

Yet another object of the present invention is to provide a method for ascertaining gene function, comprising the steps of selecting two parent plants, wherein the first plant is capable of producing paternal haploid offspring, and wherein the second plant is (1) homozygous for a first mutation that causes a first mutant phenotype and is produced by chemical mutagenesis or insertion of a first transposable element and (2) carries a second mutation produced by the insertion into its genome of a second transposable element; crossing the first plant as the female parent with the second plant as the male parent to produce a plurality of haploid $F_1$ progeny plants which contain genetic material only from the second plant; screening the haploid offspring for a plant exhibiting a second mutant phenotype characterized by a detectable change in the first mutant phenotype; and (d) cloning DNA from the mutant haploid that is associated with insertion of the second transposon.

4

A further object of the present invention is to provide a method for ascertaining gene function, comprising the steps of selecting two parent plants, wherein the first plant is capable of producing paternal haploid offspring, and the second plant is a first inbred plant that carries at least one mutation produced by chemical mutagenesis or the insertion into its genome of a transposable element, crossing the first plant as the female parent and the second plant as the male parent to produce a plurality of haploid $F_1$ progeny plants which contain genetic material only from the second plant; crossing the plurality of haploid $F_1$ progeny as the female parent with a third plant that is a second inbred to produce a plurality of $F_2$ progeny; screening the plurality of $F_2$ progeny for a mutant phenotype; and characterizing the mutant gene.

Another object of the present invention is to provide a method for the identification and selection androgenetic haploids, comprising the steps of selecting a first plant that carries the ig and Idf genes and a second plant that carries the $R_{nj}$ gene; crossing the first plant as the female parent with the second plant as the male parent; and identifying and selecting androgenetic haploid progeny that have a colored embryo.

Other objects, features and advantages of the present invention will become apparent from the following detailed description. It should be understood, however, that the detailed description and the specific examples, while indicating preferred embodiments of the invention, are given by way of illustration only. Indeed, various changes and modifications within the spirit and scope of the invention will become apparent to those skilled in the art from this detailed description.

DETAILED DESCRIPTION OF PREFERRED EMBODIMENTS

1. Definitions

In the description that follows, a number of terms are used extensively. The following definitions are provided to facilitate understanding of the invention.

A haploid plant has a single set (genome) of chromosomes and the reduced number of chromosomes (n) in the haploid plant is equal to that in the gamete.

A diploid plant has two sets (genomes) of chromosomes and the chromosome number (2n) is equal to that in the zygote.

A plant line is a group of individuals from a common ancestry and is a more narrowly defined group than a strain or variety.

Heterosis or hybrid vigor is the increased vigor, growth, size, yield or function of a hybrid progeny over the parents that results from crossing genetically unlike organisms.

A hybrid is the first generation offspring of a cross between two individuals differing in one or more genes.

An inbred is a pure line usually originating by self-pollination and selection.

A quantitative character is a character that is influenced by a group of genes at different loci which are cumulative in their effect.

A character is the expression of a gene as revealed in the phenotype.

Phenotype is the physical or external appearance of an organism as contrasted with its genetic constitution or genotype.

An androgenetic haploid arises when the maternal nucleus is eliminated or inactivated subsequent to fertilization of the egg cell and the haploid androgenetic haploid contains in its cells the chromosome set of the male gamete only.

An enhancer sequence is any of a class of cis-acting short DNA sequences that increase transcriptional activity of a gene.

A suppressor is any secondary mutation (second-site mutation) that totally or partially restores a function lost due to a primary mutation.

A transposable genetic element or transposon is any of a class of diverse DNA segments that can insert into nonhomologous DNA (chromosomes, plasmids, virus DNA, mitochondrial and plastid DNA), exit and relocate in a reaction which is independent of the general recombination function of the host.

A structural gene is a DNA sequence that is transcribed into messenger RNA (mRNA) which is then translated into a sequence of amino acids characteristic of a specific polypeptide.

An isolated DNA molecule is a fragment of DNA that is not integrated in the genomic DNA of an organism.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

2. Overview

Androgenetic haploids are made using maize ig plants, according to the present invention. A dominant or recessive mutation is immediately revealed in the haploid generation. Pollen isolated from presumptive mutant plants is used to pollinate ig females to recover mutant alleles. In order to screen 1000 gametes, only 1000 paternal haploid plants are required instead of the 20,000 diploid plants that would be screened by conventional methods. The androgenetic haploid strategy of mutant selection significantly reduces the number of presumptive mutants that have to screened. As a result, it becomes possible to employ biochemical assays for mutant detection in addition to screening for changes in visible phenotypes. An additional benefit derives from the fact that a generation is saved by not having to self the F1 plants.

The gametes to be screened are obtained by mutagenizing pollen with EMS or by taking pollen from transposon-mutagenized plants, such as Mutator plants. In the latter case, the mutants obtained can be used to clone mutated genes.

Maize ig plants that produce androgenetic haploids at a frequency of approximately 1 to 3% of the total progeny have been identified. A method is provided for directly selecting kernels that bear androgenetic haploids.

3. Ascertaining Gene Function By Transposon Tagging and Production of Androgenetic Haploids Identifying a restriction fragment that co-segregates with the mutant allele is a key step in the isolation of a gene by transposon tagging. Typically, a transposon insertional event is present in progeny that contain the mutant allele but is absent in their siblings. Conventional methods of transposon mutant screening and selection require a selfing of wild-type plants in the $F_1$ and an examination of their progeny to identify presumptive, transposon-induced mutants. $F_2$ progeny that are homozygous wild-type plants should not contain a transposon insertion in the candidate DNA fragment associated with the mutant phenotype.

Typically, heterozygotes in the $F_2$ are selfed to produce enough seeds to verify that the candidate DNA fragment into which the transposon has inserted cosegregates with the mutation. The selfing of plants in the $F_2$ adds yet another generation to the analysis and requires the screening of additional plants. The selfing of $F_2$ plants further complicate the analysis because the transposon copy number is likely to increase upon selfing.

Pursuant to the present invention, presumptive mutant plants in the $F_1$ are used to make paternal haploids. Heterozygous $F_1$ progeny will segregate 1:1 for the mutant phenotype, and the presence or absence of the transposon can be readily determined. In addition, the molecular analysis of the paternal haploids is easier than that of $F_2$ diploids. The copy number of the transposon in the paternal haploids is likely to be significantly lower than that in the progeny produced by selfing heterozygotes in the $F_2$.

The methodology of the present invention for ascertaining gene function comprises the steps of (a) selecting two parent plants, wherein the first plant is capable of producing paternal haploid offspring, and wherein the second plant carries at least one mutation produced by the insertion into its genome of a transposable element, (b) crossing the first plant as the female parent with the second plant as the male parent to produce a plurality of haploid $F_1$ progeny plants which contain genetic material only from the second plant; (c) screening the haploid offspring for the simultaneous presence of a transposable element and a mutant phenotype which differs from a parental phenotype; and (d) cloning DNA from the mutant haploid associated with insertion of the transposon. The first plant capable of producing paternal haploid offspring can be a maize plant carrying the ig gene and the transposable element can be a member of the Mutator family. Mutator element stocks are well known to the skilled artisan, for example, S.P. Briggs, *Curr. Top. Plant Biochem. Physiol.* 6: 59 (1987).

4. Identifying Enhancers and Suppressors

Genes that interact directly or indirectly with each other can be identified by observing that a mutation in one gene reverses or enhances the pre-existing phenotype resulting from a mutation in another gene. Such interactions are easily detected using haploids. Accordingly, androgenetic haploids can be used to identify enhancers and suppressors.

In this method a mutant plant population is produced that is (i) homozygous for a first mutation that causes a first mutant phenotype induced by chemical mutagenesis or insertion of a first transposable element and (ii) carries a second mutation produced by the insertion into its genome of a second transposable element having a mutant phenotype of interest is selected by means of chemical or transposon mutagenesis. Pollen from this mutant plant population is used to pollinate plants capable of producing paternal haploid offspring to produce a plurality of haploid $F_1$ progeny plants which contain genetic material only from mutant plant population. The $F_1$ haploids are screened for offspring exhibiting a second mutant phenotype characterized by a detectable change in the first mutant phenotype. DNA from the mutant haploid associated with insertion of the transposon is cloned and characterized.

More specifically, a method for identifying enhancers and suppressors comprises the steps of (a) selecting two parent plants wherein the first plant is capable of producing paternal haploid offspring, and the second plant is (i) homozygous for a first mutation that causes a first mutant phenotype induced by chemical mutagenesis or insertion of a first transposable element and (ii) carries a second mutation produced by the insertion into its genome of a second transposable element; (b) crossing the first and second plants to produce a plurality of haploid $F_1$ progeny plants which contain genetic material only from the second plant; (c) screening the haploid offspring for a plant exhibiting a second mutant phenotype characterized by a detectable change in the first mutant phenotype; and (d) cloning the gene responsible for the observed change in first mutant phenotype. The first plant capable of producing paternal haploid offspring can be a maize plant that carries the ig gene. Transposable elements useful in transposon tagging, methods of gene identification by means of transposon tagging and maize stocks carrying the transposable elements are well known to the skilled artisan. See Dellaporta et al., "Gene Tagging with Ac/Ds Elements in Maize," THE MAIZE HANDBOOK, M. Freeling and V. Walbot (eds.), Springer-Verlag, New York, pages 219–233 (1994); K. Cone, "Transposon Tagging with Spm," THE MAIZE HANDBOOK, M. Freeling and V. Walbot (eds.), Springer-Verlag, New York, pages 240–242 (1994) and Paul S. Chomet, "Transposon Tagging with Mutator," THE MAIZE HANDBOOK, M. Freeling and V. Walbot (eds.), Springer-Verlag, New York, pages 243–249 (1994).

5. Ascertaining Gene Function Associated with Quantitative Characters

Until recently the genetic analysis of quantitative characters has foundered because of the difficulty in observing one gene segregating amongst several that affect a given trait, and because such traits must be scored on populations rather than on individuals to reduce the phenotypic variation caused by the environment. Molecular markers and recombinant inbreds have been used to address these issues but even these technical advances have serious limitations. Existing methods permit broad regions of a chromosome to be associated with a trait. The number and nature of the corresponding genes within these regions generally cannot be determined.

A conceptual alternative to the study of natural variation is to recover mutants with altered phenotypes for the character of interest. This approach has not been employed because of the large number of plants that must be screened. With the present invention, however, paternal haploids are used to eliminate the 20×-multiplier needed to sample the $F_2$. For example, a first inbred can be mutagenized and used to make paternal haploids. The haploids then are fertilized by pollen from a second inbred. The seed produced on a given haploid parent is isogenic; hence, a limited number of seeds from each plant can be screened for mutant hybrids.

The first inbred can be mutagenized by any conventional method such as chemical or transposon mutagenesis. In a preferred method, pollen from the first inbred is mutagenized by treatment with a chemical mutagen and used to make androgenetic haploids by using the mutagenized pollen in crosses to a maize plant carrying the ig gene.

In a particularly preferred method, the first inbred is homozygous for waxy (wx) while the second inbred is Wx W. Plants that are Wx Wx or Wx wx can be readily distinguished from plants that are wx wx on the basis of observable differences in endosperm characteristics. Recessive wx kernels display a uniform, marble-like opacity, and a hardness similar to that of normal kernels except when in combination with floury mutants. Cut with a blade, wx endosperm chips away evenly leaving a smooth, opaque surface while normal endosperm (in the corneous side portions of dent kernels for example) breaks unevenly and leaves an irregular, translucent surface. The starch in the cut surface of nonwaxy endosperm, whether flinty, floury, opaque, glassy or brittle, will stain blue, turning quickly to black, with iodine ($I_2$) potassioum iodide (KI) solution. On the other hand, homozygous wx (waxy) will stain reddish brown, turning soon to dark brown, with iodine ($I_2$) potassium iodide (KI) solution.

Pollen from the wx wx first inbred (inbred A) is treated with a chemical mutagen and used to pollinate maize carrying the ig gene to produce presumptively mutant, wx wx, androgenetic haploids (inbred A'). Inbred A' then is fertilized with pollen taken from a second inbred which is Wx Wx (inbred B), and pollen from inbred A in a ratio of 9:1. All the seeds produced on a given fertilized inbred A' plant will be isogenic with respect to any mutation present in that inbred A' plant. Accordingly, among every ten seeds produced on a given fertilized inbred A' plant, nine seeds will be the result of the cross A'×B and will be Wx wx, and one seed will be the result of the cross A'×A and will be wx wx. Once a mutant hybrid from the cross A'×B is identified, the mutation can be obtained immediately in the inbred A background by selection of wx wx seed produced on the same inbred A' plant that gave rise to the Wx wx mutant of interest. The wx wx seed can be germinated and the plant used in crosses for genetic mapping and characterization of the mutant allele.

This method can be used to ascertain gene function associated with a variety of different quantitative characters. The hybrid population can be screened for mutations in the first inbred that reduce hybrid vigor or growth under high plant densities. Alternatively, the hybrid population can be screened for mutations in the first plant that lead to increased salt tolerance, drought tolerance, hybrid vigor or growth under conditions of high plant density.

A method for ascertaining genes that control quantitative traits thus comprises (a) selecting two parent plants, wherein the first plant is capable of producing paternal haploid offspring, and the second plant is a first inbred plant that carries at least one mutation produced by chemical mutagenesis or the insertion into its genome of a transposable element; (b) crossing the first and second plants to produce a plurality of haploid $F_1$ progeny plants which contain genetic material only from the second plant; (c) crossing the plurality of haploid $F_1$ progeny as the female parent to a third plant which is a second inbred to produce a plurality of $F_2$ progeny; (d) screening the plurality of $F_2$ progeny for a mutant phenotype; and (e) characterizing the mutant gene. The method can be used to ascertain gene function associated with the control of heterosis or ability of a plant to grow efficiently at high stand density wherein the first plant capable of producing paternal haploid offspring is a maize plant that carries the ig gene.

6. Identification and Selection of Androgenetic Haploids

A method for the direct selection of androgenetic haploids is provided. In this method the $R_{nj}$ gene is only expressed in androgenetic haploids and therefore the androgenetic haploids are identified and selected as seeds with colored embryos.

The present method for the direct selection of androgenetic haploids overcomes the disadvantage of using $R_{nj}$ in the female for selection of colorless haploids. Instead, a method is provided for selecting haploid embryos that have color. There is a high frequency of misclassification when scoring for the absence of color because of variation in the extent of synthesis of the pigment during development. For example, diploid kernels may fail to produce detectable pigment depending upon the environmental conditions and genetic background of the plant. In addition, the $R_{nj}$ gene causes pigment to be produced on a small part of the embryo which is the embryo axis and consequently the pigmentation is difficult to detect through the overlying pericarp tissue.

The plant from which the androgenetic haploid is to be constructed is made homozygous for the $R_{nj}$ gene. The female ig parent that is capable of producing androgenetic haploids is made homozygous for the Idf or indeterminate-diffuse gene. The Idf gene suppresses expression of the $R_{nj}$ gene and anthocyanin pigment formation leading to production of seeds with white embryos. A plant that is $R_{nj} R_{nj}$ is crossed as the male parent with a plant that carries the ig gene and is Idf Idf. Only the androgenetic haploid progeny will not carry the Idf gene and consequently only the androgenetic haploid progeny will have colored embryos. It is therefore possible to detect haploid progeny by screening for colored embryos. For example, the screening process can be done mechanically and colored embryos detected and selected by means of an electric eye that detects reflected light of certains wavelengths.

A method for the identification and selection androgenetic haploids comprises the steps of (a) selecting a first plant that carries the ig and is homozygous for the Idf gene and a second plant that is homozygous for the $R_{nj}$ gene; (b) crossing the first plant as the female parent with the second plant as the male parent; and (c) identifying and selecting androgenetic haploid progeny that have a colored embryo.

The present invention, thus generally described, will be understood more readily by reference to the following examples, which are provided by way of illustration and are not intended to be limiting of the present invention.

EXAMPLE 1

Detection and Isolation of Genes Which Contribute to Heterosis

To isolate mutations in genes which contribute to heterosis, pollen from the waxy mutant inbred AM21WX, was treated with the mutagen ethylmethane sulfonate (EMS) using methods well known to the skilled artisan. See Neuffer et al., *Maydica* 22: 21 (1977) or G.F. Sprague and J. W. Dudley, eds., CORN AND CORN IMPROVEMENT, American Society of Agronomy, Madison, 3rd edition (1988). The mutagenized pollen was used to fertilize eggs of igigWxWx mutant plants. Kernels bearing paternal haploid embryos were selected on the basis of embryo color and planted.

The haploids were fertilized with a mixture of pollen from the inbreds HD93 and AM21WX. The waxy kernels produced by fertilization with AM21WX pollen were selected and set aside. The vitreous, non-waxy kernels produced by fertilization with HD93 pollen were selected and grown for mutant selection. Observations are made to identify progeny obtained from non-waxy kernels that carry mutations that affect heterosis such as yield and time required for maturation.

Mutations that are inherited by the haploid embryo which affect heterosis of the HD93/AM21WX are recovered from the waxy seed produced on the haploid plant. The waxy seed are the inbred AM21WX/AM21WX that are heterozygous for the mutation. The inheritance of the mutant allele can be followed by repeating the heterosis assay. If the mutation causes a phenotype which can be scored directly on mutant plants, then the gene is cloned by transposon tagging methods.

EXAMPLE 2

Ig-Induced Haploids and Identification of Transposon-Tagged Genes

A diverse collection of heterozygous, Mutator-active lines was used to pollinate igig plants. Five thousand kernels bearing paternal haploid embryos were selected. Plants from the kernels are screened for the loss of disease resistance to maize pathogens such as *Fusarium moniliforme*, *Cochliobalus carbonum*, *Erwinia stewartii*, or maize dwarf mosaic virus. Alternatively, the loss of specific stress gene function such as pathogen defense genes or peroxidase is screened.

Mutant plants are pollinated by a non-mutant inbred to recover the mutant allele. The heterozygous progeny are grown and self-pollinated or crossed to an igig line to produce progeny in which the segregating mutation can be observed. DNA from the segregating progeny is examined by Southern blot analysis using Mu-specific hybridization probes to identify a Mu element that cosegregates with each tagged mutant locus.

As many different outcrossed segregating lines should be examined as possible. In addition, it is useful to examine the population utilizing a number of different restriction enzymes since segregating fragments may be obscured by other Mu-homologous elements. DNA from the parent lines is included in the Southern blot analyses because a cosegregating fragment should not be present in the parental plant. Once a cosegregating fragment is identifed, additional analyses with a different and larger population set should be performed.

Once a cosegregating band is identified, cloning or PCR is used to obtain flanking unique sequence. This flanking probe is then used to prove the locus is responsible for the mutant phenotype. For example, identification of DNA rearrangements, insertions, or deletions at the locus of independently generated alleles demonstrates the clone is, or is in close proximity to, the locus of interest.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for ascertaining gene function, comprising the steps of:
    (a) selecting two maize parent plants, wherein the first plant is capable of producing paternal haploid offspring and carries the indeterminate gametophyte (ig) gene, and wherein the second plant carries at least one mutation produced by the insertion into its genome of a transposable element;
    (b) crossing the first plant as a female parent with the second plant as the male parent to produce a plurality of haploid $F_1$ progeny plants which contain genetic material only from said second plant;
    (c) screening said haploid offspring for the simultaneous presence of a transposable element and a mutant phenotype which differs from a parental phenotype; and
    (d) cloning DNA from said mutant haploid that is associated with insertion of the transposon.

2. A method according to claim 1, wherein said transposable element is a member of the Mutator family.

3. A method for ascertaining gene function, comprising the steps of:

(a) selecting two parent maize plants, wherein the first plant is capable of producing paternal haploid offspring and carries the ig gene, and wherein the second plant is (i) homozygous for a first mutation that causes a first mutant phenotype and is produced by chemical mutagenesis or insertion of a first transposable element and (ii) carries a second mutation produced by the insertion into its genome of a second transposable element;

(b) crossing said first plant as the female parent with the second plant as the male parent to produce a plurality of haploid $F_1$ progeny plants which contain genetic material only from said second plant;

(c) screening said haploid offspring for a plant exhibiting a second mutant phenotype characterized by a detectable change in the first mutant phenotype; and (d) cloning DNA from said mutant haploid that is associated with insertion of said second transposon.

4. A method for ascertaining gene function, comprising the steps of:

(a) selecting two parent maize plants, wherein the first plant is capable of producing paternal haploid offspring and carries the ig gene, and the second plant is a first inbred plant that carries at least one mutation produced by chemical mutagenesis or the insertion into its genome of a transposable element, (b) crossing said first plant as the female parent and the second plant as the male parent to produce a plurality of haploid $F_1$ progeny plants which contain genetic material only from said second plant;

(c) crossing said plurality of haploid $F_1$ progeny as the female parent with a third plant that is a second inbred to produce a plurality of $F_2$ progeny;

(d) screening said plurality of $F_2$ progeny for a mutant phenotype; and (e) characterizing the mutant gene.

5. A method for the identification and selection of androgenetic maize haploids, comprising the steps of:

(a) selecting a first plant that carries the ig and indeterminate diffuse (Idf) genes and a second plant that carries a colored embryo gene;

(b) crossing said first plant as the female parent with the second plant as the male parent; and (c) identifying and selecting androgenetic haploid progeny that have a colored embryo.

6. The method according to claim 5, wherein said colored embryo gene is the $R_{nj}$ gene.

7. The method according to any one of claims 1, 3 or 4 wherein said first plant carries the Idf gene and said second plant carries a colored embryo gene.

8. The method according to claim 7, wherein said colored embryo gene is the $R_{nj}$ gene.

\* \* \* \* \*